United States Patent [19]

Boxer

[11] 4,155,364
[45] May 22, 1979

[54] URINARY CATHETER

[75] Inventor: Richard J. Boxer, Los Angeles, Calif.

[73] Assignee: The Regents of the University of California, Berkeley, Calif.

[21] Appl. No.: 849,195

[22] Filed: Nov. 7, 1977

[51] Int. Cl.² ............................................. A61M 25/00
[52] U.S. Cl. ............................ 128/349 B; 128/DIG. 9
[58] Field of Search ............... 128/348, 349 R, 349 B, 128/349 BV, 350-351, DIG. 9

[56] References Cited

U.S. PATENT DOCUMENTS

| 3,593,713 | 7/1968 | Bogoff et al. | 128/349 B |
| 3,630,206 | 12/1971 | Gingold | 128/349 B |

FOREIGN PATENT DOCUMENTS 156901 2/1954 Sweden .............................. 128/DIG. 9

Primary Examiner—E. H. Eickholt
Attorney, Agent, or Firm—Jessup & Beecher

[57] ABSTRACT

A catheter assembly for placement in the bladder and particularly for use in patients with a restricted or traumatized urethra. The catheter assembly comprises a flexible filiform and a flexible follower detachably connected to the end of the filiform. A modified urinary catheter of flexible material with an extra hole in a tapered tip is used. The hole in the end of the catheter is restricted so that the connecting end of the follower may be easily pushed through, but the remaining portion of the follower is gripped securely.

8 Claims, 4 Drawing Figures

URINARY CATHETER

BACKGROUND OF THE INVENTION

This invention relates to catheters and in particular relates to a new urinary catheter assembly which permits placement in difficult catherization and/or situations,.

In situations such as urethra strictures or restrictions, high bladder neck, or benign or malignant prostatic hypertrophy, causing difficult catheterization, the current procedure is to insert a filiform and a follower and leave the follower in place for a period of time before placing a urinary catheter. The result can be patient discomfort from the follower, bleeding, and possibly a severe infection.

In these situations, passing a standard urinary catheter can traumatize the urethra. Often a urologist is called to see a patient after several attempts to catheterize the patient have failed, resulting in a severely traumatized urethra. A metal Council catheter guide may be helpful to the urologist, but this can further traumatize the urethra. A Council guide then must be used by an experienced person who is almost never available in an emergency room or hospital ward.

SUMMARY OF THE INVENTION

The purpose of the present invention is to provide a catheter assembly and particularly a urinary catheter assembly which can solve the aforementioned problems, permitting placement of a catheter in difficult situations.

The method of the present invention is to first place a flexible filiform having a connector on one end which is detachably secured to a hollow flexible extra-long follower. The follower is inserted into the bladder with the filiform until a back flow of urine through an aperture in the follower indicates complete placement. This effectively opens any restriction or traumatized portion of the urethra. The follower and filiform is then withdrawn until the connection is exposed. The follower may then be disconnected easily from the filiform and inserted through the central passageway of a modified Foley catheter. The catheter has a thickened tapered tip having a restricted hole in the end through which the relatively hard end of the follower may be pushed, but through which the remaining portion of the follower will not pass. The restricted thickened portion of the modified Foley catheter thus grips the follower. The connection of the end of the follower may then be reattached to the filiform and the entire assembly passed through the urethra into the bladder. The Foley catheter balloon is then expanded to hold it in place and the follower and filiform withdrawn. The invention can be used after possibly one or two attempts to place a standard catheter fails. It is believed that the present invention allows placement of a catheter in difficult cases without need for calling a specialist, such as a urologist at a great saving to the patient.

The catheter assembly is a disposable one-unit, self-contained, proper-fitting, flexible filiform and follower with a catheter that can be easily used by a trained practitioner, allowing a non-specialist to catheterize even the most difficult patient. The filiform is constructed of a disposable flexible material and has a female socket for attachment to a male threaded connector attached to the end of the flexible, disposable, extra-long follower. The flexible catheter, as described previously, is a modified Foley catheter having a thickened tapered resilient end with a restricted opening for securely gripping the follower after it has passed through the central passageway of the catheter.

The essence of the invention is the provision of a completely disposable catheter assembly which permits placement of a catheter in the urinary tract in the most difficult of situations without the need for calling a specialist. The filiform is flexible and disposable and is detachably connected to a hollow flexible and disposable follower which may be inserted through a specially designed catheter after initial placement of the filiform and follower.

It is one object of the present invention to provide a catheter assembly for placement in the urinary tract in difficult situations.

Another object of the present invention is to provide a catheter assembly which may be placed in difficult situations without the need for calling a specialist.

Another object of the present invention is to provide a catheter assembly and method having a filiform and detachable follower for use in restricted or traumatized urethras.

Still another object of the present invention is to provide a catheter assembly having a modified catheter for use with a detachable filiform-follower assembly.

Other objects and novel features of the invention will become apparent from the following detailed description of the invention when considered in conjunction with the accompanying drawings wherein like reference numbers identify like parts throughout.

DETAILED DESCRIPTION OF THE PREFERRED EMBODIMENT

Figure 1:
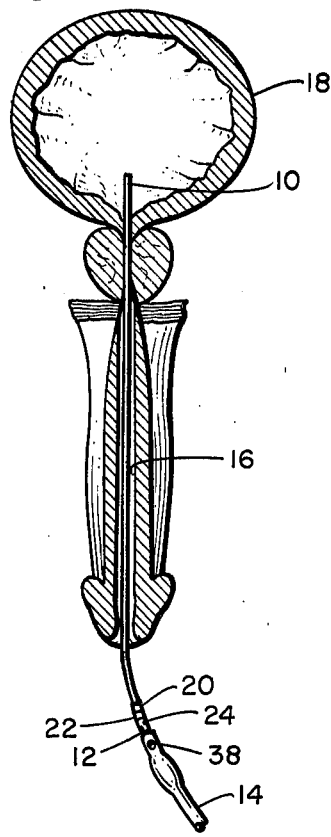
FIG. 1 illustrates the catheter assembly and method of use.

The method of placing the catheter assembly in difficult situations, such as restricted or traumatized urethra, is illustrated in FIG. 1, in which the catheter assembly is comprised of a flexible filiform 10 detachably secured to a follower 12 and a urinary catheter 14. In FIG. 1 the filiform 10 is shown inserted in the urethra 16 and extending into the bladder 18.

Figure 3:
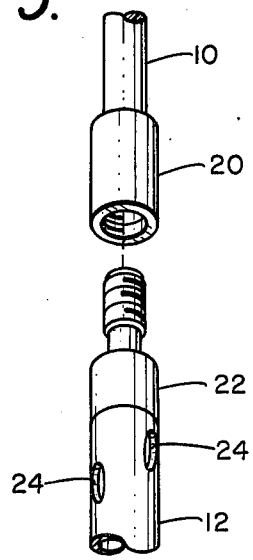
FIG. 3 is a detailed view of the connecting portion of the filiform-follower.

The filiform 10 and follower 12 are detachably connected as illustrated in the detail of FIG. 3. The filiform 10 has a female socket 20 having threads for securing the follower 12 by a male threaded connector 22. Apertures 24 in the hollow follower 12 permit backflow of fluid through the follower confirming placement of assembly in the bladder 18.

Figure 4:
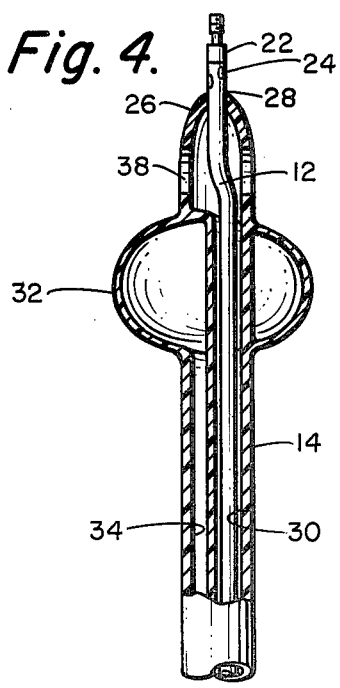
FIG. 4 is a sectional view of the catheter assembly taken at 4—4 of FIG. 2.

The sectional view of FIG. 4 illustrates the modification of a typical urinary catheter 14, sometimes called a Foley catheter, in which the tip 26 is provided with a hole 28 through which the connector 22 of the follower 12 may pass. The tip 26 of the catheter 14 has a strengthened or thickened resilient wall and the aperture 28 is restricted to securely grip the flexible portion of the follower 12 below the connector 22. The connector 22 may be constructed of a metal or some other rigid material, such as a rigid plastic, so that it may be easily passed or pushed through the restricted hole 28 in the end of the catheter 14. As can be seen, the extra-long follower 12 passes through a central passageway 30 of the flexible catheter 14. The catheter is of a flexible and disposable material and is provided with the usual inflatable balloon portion 32 connected to a suitable passageway 34 for inflation by a pump or syringe 36, as shown in FIG. 2.

The catheter assembly is used by first attaching the follower 12 to the filiform 10 and then inserting the filiform through the urethra 16 until a backflow through apertures 24 indicates placement of the follower in the bladder 18. This initial step is not shown but can be easily visualized in FIG. 1. The next step is to then withdraw the filiform-follower assembly 10, 12, until the connector 20,22 is exposed. The follower 12 may then be disconnected from the filiform 10 and inserted in the catheter 14 as illustrated in FIG. 4. The follower being quite flexible is pushed through the catheter 14 until rigid connector 22 passes through the restricted aperture 28, firmly gripping the flexible follower 12. The connector 22 is then reattached to the socket 20 on the filiform 10.

Figure 2:
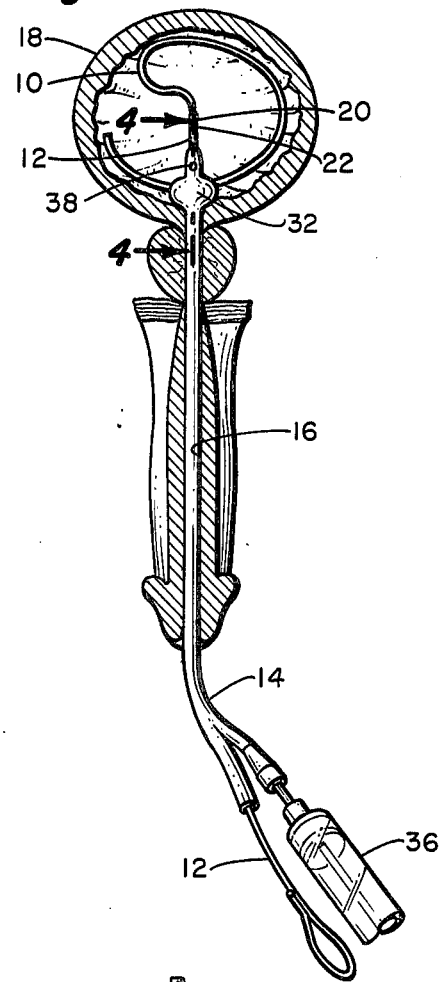
FIG. 2 illustrates the catheter assembly after placement in the bladder.

The entire assembly may then be inserted through the urethra into the bladder, as illustrated in FIG. 2. The bulb portion 32 of catheter 14 may then be inflated by the pump or syringe 36, securing the catheter 14 in place in the urinary tract. The filiform-follower assembly 10,12 may then be withdrawn from the catheter 14, leaving the catheter properly placed in the bladder 18. The catheter 14 has the usual aperture 38 in the side wall which allows backflow of urine to also indicate that it has been properly placed. If desired, apertures 24 in the follower 12 may be plugged or kept within the restriction or hole 28 in the catheter 14 so that the backflow of urine through the aperture 38 in the catheter 14 is confirmed.

Thus there has been described a unique catheter assembly and method for placement of a catheter in difficult situations, such as a urethral stricture, high bladder neck, or benign or malignant prostatic hypertrophy. The novel catheter assembly is flexible and has a filiform and follower which go within an indwelling modified Foley catheter allowing the soft indwelling catheter to remain in the bladder after the filiform and follower are removed. The catheter assembly is fast, safe, disposable and can be used by a non-specialist trained practitioner. It provides considerably more versatility than previous catheter devices.

Obviously, many modifications and variations of the present invention are possible in light of the above teachings. It is therefore to be understood that the full scope of the invention is not limited to details disclosed herein and may be practiced otherwise than as specifically described.

What is claimed is:

1. A method of catheterizing a restricted or traumatized urethra comprising:
   inserting a flexible firm filiform partially into the bladder through the urethra;
   connecting a flexible follower tube to the end of said filiform;
   inserting the remaining portion of the filiform into the bladder with said follower until backflow of urine indicates the follower is properly placed to dilate the urethra;
   withdrawing the follower until the connection between the follower and filiform is exposed;
   disconnecting the follower from the filiform leaving the filiform placed;
   introducing the follower into a catheter having a hole in its tip until only the connecting end of the follower is exposed through said hole;
   reconnecting the follower-catheter assembly to the exposed end of the filiform;
   inserting the follower-catheter assembly into the bladder with the filiform;
   inflating the catheter tip in the bladder; and
   withdrawing the follower and filiform through the catheter leaving the catheter placed.

2. The method according to claim 1 wherein the connection step comprises joining male and female threaded connectors on said filiform and follower.

3. The method according to claim 1 wherein said step of introducing the follower in the catheter comprises:
   inserting a male threaded end of said follower through a central passageway of said catheter.

4. The method according to claim 3 wherein said hole in end of said catheter is restricted to grip said follower.

5. A catheter assembly for insertion into a restricted or traumatized urethra comprising:
   a flexible filiform;
   a hollow flexible follower;
   connecting means for detachably connecting one end of said follower to said filiform;
   a flexible catheter means having a central passageway through which said follower is inserted;
   a restricted aperture in the end of said catheter through which said connecting end of said follower may pass before connecting to said filiform.

6. The catheter assembly according to claim 5 wherein said connecting means comprises a male-female threaded connector on the respective ends of said filiform and follower.

7. The catheter assembly according to claim 5 wherein the end of said catheter adjacent to said aperture has a tapered and stiffened wall construction to securely grip the end of said follower adjacent to said connecting means.

8. The catheter assembly according to claim 7 wherein said catheter has at least one hole in the side wall near said tip communicating with said central passageway.

* * * * *